United States Patent [19]
Levin

[11] Patent Number: 4,569,071
[45] Date of Patent: Feb. 4, 1986

[54] HAND TOOL FOR HOLDING A DENTAL XERORADIOGRAPHIC CASSETTE

[76] Inventor: Martin Levin, 9111 Burdette Rd., Bethesda, Md. 20817

[21] Appl. No.: 593,850

[22] Filed: Mar. 27, 1984

Related U.S. Application Data

[63] Continuation-in-part of Ser. No. 569,619, Jan. 10, 1984, abandoned.

[51] Int. Cl.[4] .............. A61B 6/14; G03B 42/02; A61C 3/14; B25B 7/02
[52] U.S. Cl. .................. 378/168; 378/169; 378/181; 378/205; 433/159; 83/425 ; 83/420
[58] Field of Search ............ 378/167, 168, 169, 170, 378/177, 181, 205; 81/420, 425 R, 425 A; 269/257; 433/159

[56] References Cited

U.S. PATENT DOCUMENTS

| | | | |
|---|---|---|---|
| 1,465,516 | 8/1923 | Hallenberg | 378/170 |
| 1,576,477 | 3/1926 | Wiens | 378/168 |
| 3,169,034 | 2/1965 | Epstein | 81/420 |

Primary Examiner—Richard L. Schilling
Attorney, Agent, or Firm—Howard L. Rose

[57] ABSTRACT

A handtool for holding a dental xeroradiographic cassette, the handtool comprising a first elongated member having a first handle portion at one end thereof and a first beak at the opposite end thereof; a second elongated member having a second handle at one end thereof and a second beak at the opposite end thereof; and said first elongated member and said second elongated member being pivotally coupled, said beaks being pivoted toward or away from each other by selectively squeezing together or spreading apart said two handles; said first beak including a first surface facing said second beak; and said second beak including (a) a first member having a second surface facing said first beak and (b) a protrusion extending toward said first beak, said first member and said protrusion defining an elbow-shaped cross-section along a longitudinal segment of at least a length L; wherein said first beak and said segment of at least a length of said second beak together define a slit C-shaped transverse cross-section when said beaks are pivoted together; said first surface and said second surface being pivotable toward each other to engage the cassette therebetween.

21 Claims, 4 Drawing Figures

HAND TOOL FOR HOLDING A DENTAL XERORADIOGRAPHIC CASSETTE

RELATED APPLICATION

This is a continuation-in-part application of U.S. Ser. No. 569,619 filed 1/10/84, now abandoned.

FIELD OF THE INVENTION

The present invention relates to hand tools for holding a dental xeroradiographic cassette.

SUMMARY OF THE INVENTION

In accordance with the invention, a hand tool for holding a dental xeroradiographic cassette is provided. Specifically, the hand tool includes two pivotally coupled elongated members, each elongated member having a beak at one end thereof and a handle at the other end. The beaks pivot toward each other by squeezing the handles together. The beaks are shaped so that as the beaks pivot toward each other they together define a C-shaped cross-section along a length L. The upper and lower portions of the C represent jaws which engage the cassette therebetween.

Preferably, one beak has an elbow-shaped transverse cross-section and includes (a) a first laterally extending member having a surface which faces an opposite surface on the other beak and (b) a protrusion extending from the one beak toward the other beak. The cassette is engageable between the opposite surfaces as the beaks are pivoted toward each other.

According to the invention, the protrusion serves the define a minimum spacing between the two opposite surfaces. That is, there is a minimum spacing when the protrusion on the one beak abuts the other beak. Furthermore, the protrusion provides a contour against which an edge of the cassette can rest when inserted between the two opposite, facing surfaces.

Moreover, a clamp is provided for locking the pivotally coupled members in place when the xeroradiographic cassette is engaged between the two beaks.

It is thus an object of the invention to provide a hand tool for easily and firmly holding a dental xeroradiographic cassette that is to be inserted into the mouth of a patient. In addition, it is another object to engage such a cassette of thickness t between two opposite facing surfaces which are movable to be substantially parallel and to have a spacing defined therebetween corresponding to the cassette thickness.

It is yet another object of the invention to provide a protrusion which serves to define a minimum spacing between the two opposite, facing surfaces and to define a contour against which an edge of a xeroradiographic cassette can rest.

Finally, it is an object to enable a dental practitioner to place and hold a xeroradiographic cassette in the mouth of a patient without requiring the practitioner to hold or position the cassette when it has been inserted in the mouth.

BRIEF DESCRIPTION OF THE DRAWINGS

FIG. I is a plan view of a hand tool according to the invention.

FIG. II is a transverse cross-section view of the hand tool of FIG. I taken along line II—II.

Figure 1:
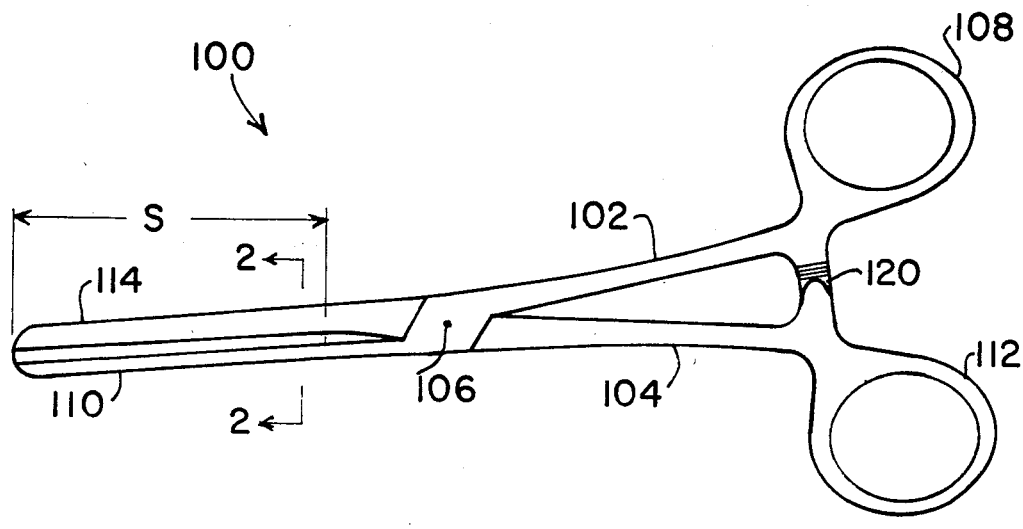
Figure 2:
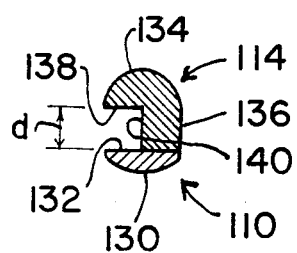
Figure 3:
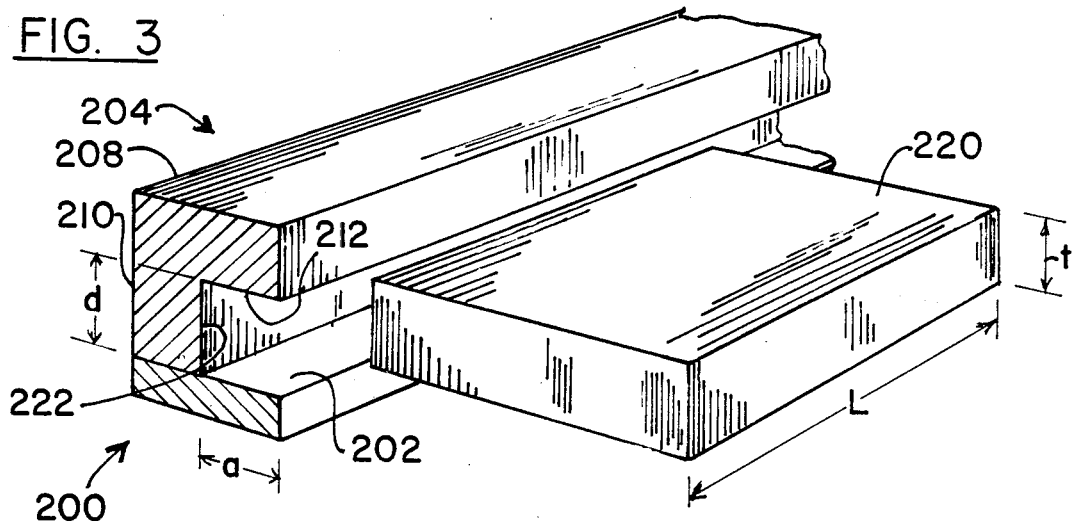

FIG. III is an upper right perspective view of an alternative beak in a hand tool according to the invention FIG. IV is a perspective view of an alternative embodiment of beaks according to the invention, with the handle portions omitted.

DESCRIPTION OF THE INVENTION

In FIG. I, a hand tool 100 is shown including two elongated members 102 and 104 pivotally coupled by a pin 106. The first elongated member 102 has a handle 108 at one end and a beak 110 at the other end thereof. The second elongated member 104 has a handle 112 at one end and a beak 114 at the other end. When the handles 108 and 112 are squeezed together the beaks 110 and 114 pivot toward each other in a scissor-type action. Similarly, spreading the handles 108 and 112 apart results in pivoting the beaks 110 and 114 apart. A clamp 120 is provided to mechanically lock the handles 108 and 112 in respective positions—the beaks 110 and 114 also being held in fixed relative position thereby. The clamp 120 is a typical mechanical lock employed in clamps, forceps, and like devices.

Examining the beaks 110 and 114 in greater detail, reference is now made to both FIG. I and FIG. II. As illustrated in FIG. I, the beaks 110 and 114 extend longitudinally with a segment S thereof being specifically identified. The cross-sections of the beaks 110 and 114 along the segment S are shown in FIG. II.

Specifically, beak 110 has a cross-section along the segment S bounded by an arcuate outer surface 130 and an inner surface 132 that faces the beak 114. The surface 132 is shown to be flat, and extends beyond the segment S toward the pivot pin 106.

The beak 114 has an elbow-shaped cross-section and includes a laterally extending member 134 and a protrusion 136 extending from the member 134 toward the beak 110. The member 134 includes a surface 138 which faces the surface 132 along a longitudinal strip thereof. The protrusion 136 is also positioned opposite the beak 110 so that the protrusion 136 abuts the beak 110 when the beaks 110 and 114 are pivoted closed. In FIGS. I and II, the beaks 110 and 114 are pivoted closed. In this closed position, the beaks 110 and 114 provide a split C-shaped cross-section extending longitudinally along the segment S. In this regard, the surface 138 and the longitudinal strip of surface 132—which are opposite and face each other—have a spacing d therebetween. Or, in other words, a longitudinally extending, lateral slot is thereby provided.

The surfaces 132 and 138, in the FIGS. I and II embodiment, are flat and lie in parallel planes. The surfaces 132 and 138 are preferably rough, including ribs or waffling thereon. The spacing d is less than or approximately equal to the thickness of a xeroradiographic cassette (not shown). Accordingly, when the beaks 110 and 114 are pivoted apart, the cassette can be inserted between the surfaces 132 and 138 and against a surface 140 of the protrusion 136. After insertion of the cassette, the beaks 110 and 114 are pivoted together to engage the cassette therebetween. When the thickness of the cassette is approximately equal to d, the beaks 110 and 114 are pivoted closed—with the protrusion 136 abutting the beak 110—and the cassette is sandwiched between the surfaces 132 and 138.

In FIG. II, it is noted that the C-shaped cross-section is inverted and that it has an arcuate periphery with a three-sided, square cornered interior. The term "C- shaped" it should therefore be recognized is used in a general sense and may include a curved C-shape, a square-cornered C-shape, or the like.

Referring to FIG. III, an alternative structure for beaks disposed along elongated members as illustrated in FIG. I is shown. In particular, a beak 200 is shown having a rectangular cross-section and a flat surface 202 which faces a second beak 204. The beak 204 has a first, laterally extending member 208 from which a protrusion 210 extends toward beak 200. The member 208 has a surface 212 facing the surface 202 along a longitudinal strip thereof of width a. Surfaces 202 and 212 are rough, including ribbing, waffling or the like thereon to enhance engagement of the cassette 220 therebetween. As in the embodiment of FIG. II, the beaks 200 and 204 are pivoted closed to provide (a) a spacing d between the surface 212 and the strip of surface 202 and (b) and a C-shaped cross-section.

The surface 212 and the strip of surface 202 act as jaws between which a dental xeroradiographic cassette 220 can be inserted and engaged. The cassette 220 has a length L in one dimension thereof and has a thickness t which is greater than or approximately equal to d.

If the cassette thickness t is approximately equal to d, the cassette 220 is engaged when the beaks 200 and 204 are pivoted closed. If the thickness t exceeds the distance d, the inserted cassette 220 is engaged before the beaks 200 and 204 are pivoted closed. In either case, a clamp or other mechanical lock such as clamp 120 of FIG. I is provided to lock the beaks 200 and 204 in position with cassette 220 therebetween. When the cassette thickness t is approximately equal to d, pivoting the beaks 200 and 204 closed results in engagement but not sufficient pressure to damage the cassette 220.

Also in FIG. III it is observed that the protrusion 210 has a contour 222 against which the cassette 220 can rest when inserted and engaged between the beaks 200 and 204. In this preferred form, the protrusion 210 extends longitudinally at least the length L of the cassette 220. If desired, however, the protrusion 220 may extend longitudinally for a shorter distance. In either case, the protrusion 210 serves (a) to define the spacing d between the beaks 200 and 204 when pivoted closed and (b) as a contour surface 222 against which the cassette 220 can rest when engaged. In a specific embodiment, the contour 222 conforms to the shape of the cassette edge resting thereagainst.

Referring to FIG. IV, an alternative arrangement of the invention is shown. A first beak 300 has an elbow-shaped cross-section including a member 302 and a protrusion 304 extending toward a second beak 306. The second beak 306 similarly includes a member 308 and a protrusion 310 aligned to abut the protrusion 304 when the beaks 300 and 306 are pivoted together. The members 302 and 308 have surfaces which face each other and between which a cassette 320 of length L' is engaged when the beaks 302 and 308 are pivoted toward each other. The beaks 302 and 308 extend along respective longitudinal segments—both of which are of equal length S' in FIG. IV although this is not required. Also in FIG. IV, the length S' is less than the length L'. The length of the longitudinal segments need be long enough to provide firm cassett engagement as the beaks 302 and 308 are pivoted toward each other. As in previous embodiments, the spacing d' between facing surfaces of the beaks 302 and 308 is approximately equal to the thickness t' of the cassette 320. Also, as in the previous embodiments, although the protrusions 304 and 310 define a curved surface against which the cassette 320 lies, the protrusions 304 and 310 may alternatively define a flat surface such as that illustrated in FIG. III. That is, a curved (or otherwise specially contoured) c-shaped cross-section or a squared c-shaped cross-section may be defined by the protrusions 304 and 310.

In accordance with the invention, the hand tool 100—including either beak construction—comprises medical grade, autoclavable stainless steel.

Furthermore, it is preferred that the distance d be 4 millimeters and that the segment S be 4 centimeters to enable the beaks to receive and engage a standard dental xeroradiographic cassette, such as the commercial, available Xerox 110 dental xeroradiographic cassette. The width of the strip "a" is selected to enable firm engagement of the cassette between the opposite, facing surfaces of the beaks.

Other improvements, modifications, and embodiments will become apparent to one of ordinary skill in the art upon review of this disclosure. Such improvements, modifications and embodiments are considered to be within the scope of this invention as defined by the following claims.

I claim:

1. A hand tool for holding a dental xeroradiographic cassette having a side of length L and a thickness t, the hand tool comprising:
   a first elongated member having a first handle portion at one end thereof and a first elongated beak extending substantially in the direction of elongation said member at the opposite end thereof;
   a second elongated member having a second handle at one end thereof and a second elongated beak extending substantially in the direction of elongation of said second member at the opposite end thereof; and
   means for pivotally coupling said first elongated member and said second elongated member, said beaks being pivoted toward or away from each other by selectively squeezing together or spreading apart said two handles;
   wherein said first beak includes a longitudinally extending first surface that faces said second beak; and
   wherein said second beak includes (a) a first laterally extending member having a second surface facing said first surface along a longitudinal strip thereof, and (b) a protrusion extending from said first member toward said first beak; and
   wherein said protrusion abuts said first surface to define a spacing of distance d that is no greater than t between said second surface and said longitudinal strip, responsive to said beaks being pivoted closed thereby defining an elongated slot;
   one peripheral edge of the cassette being engageable between said second surface and said longitudinal strip in said slot where the cassette projects therefrom when said first and second beaks are pivoted toward each other with the cassette disposed therebetween and removable upon pivoting said first and second beaks apart.

2. A hand tool according to claim 1 wherein said second surface and said first surface along said longitudinal strip thereof lie parallel to each other when said beaks are pivoted closed.

3. A hand tool according to claim 2 wherein said second surface and said longitudinal strip are each flat, rectangular, and substantially coextensive with each other.

4. A hand tool according to claim 3 wherein
said protrusion extends longitudinally, adjacent said second surface;
said second surface, said longitudinal strip, and said protrusion defining a transverse slot into which the cassette is engageable when said beaks are pivoted together where said slot has cross-sectional linear dimensions substantially less than the linear length of the beaks.

5. A hand tool according to claim 4 further comprising:
clamp means for locking said first beak in a selected position relative to the position of said second beak.

6. A hand tool according to claim 4 wherein said distance d is substantially equal to the thickness t of the cassette.

7. A hand tool according to claim 6 wherein
the cassette is engageable (a) between said second surface and said longitudinal strip and (b) against said protrusion;
said protrusion being contoured to conform to the peripheral edge of the cassette enabling the cassette to lie thereagainst.

8. A hand tool according to claim 1 wherein
the cassette is engageable (a) between said second surface and said longitudinal strip and (b) against said protrusion;
said protrusion being contoured to conform to the peripheral edge of the cassette enabling the cassette to lie thereagainst.

9. A hand tool according to claim 7 wherein the distance d is approximately 4 mm and the length L is approximately 4 cm.

10. A hand tool for holding a dental xeroradiographic cassette, the hand tool comprising:
a first elongated member having a first handle portion at one end thereof and a first beak at the opposite end thereof extending substantially colinearly with said member;
a second elongated member having a second handle at one end thereof and a second beak at the opposite end thereof extending substantially colinearly with said second member;
means for pivotally coupling said first elongated member and said second elongated member, said beaks being pivoted toward or away from each other by selectively squeezing together or spreading apart said two handles;
said first beak including a first substantially planar surface facing said second beak; and
said second beak including (a) a first member having a second surface facing said first beak and (b) a protrusion extending toward and adapted to abut said first planar surface of said first beak, said first member and the protrusion extending therefrom defining an elbow-shaped cross-section along a first longitudinal segment;
wherein said first beak and said first longitudinal segment of said second beak together define a split C-shaped transverse cross-section comprising a slot when said beaks are pivoted together where the cross-section is of substantially smaller linear dimensions than the linear length of said first and second beaks;
said first surface and said second surface being pivotable toward each other to engage the cassette therebetween.

11. A hand tool according to claim 10 wherein
said first surface and said second surface are parallel when pivoted to engage the casette therebetween; and
wherein said first surface and said second surface are pivoted to a closed position with said protrusion abutting said first surface when said first surface and said second surface are pivoted to engage the cassette therebetween.

12. A hand tool according to claim 11 further comprising:
clamp means for mechanically locking said two members in a selected position.

13. A hand tool according to claim 12 wherein said elongated members and coupling means comprise autoclavable stainless steel.

14. A hand tool according to claim 10 wherein said elbow-shaped cross-section is a square-cornered, elbow-shaped cross-section and wherein said C-shaped cross-section is a square-cornered C-shaped cross-section.

15. A hand tool according to claim 10 wherein said first surface and said second surface each comprises a rough surface.

16. A hand tool according to claim 10
wherein said first beak includes (a) a second member having a third surface facing said second surface and (b) a protrusion extending from said second member, said second member and the protrusion extending therefrom defining an elbow-shaped cross-section along a second longitudinal segment; and
wherein the protrusion extending from said first member and the protrusion extending from said second member are aligned to abut each other in response to said beaks being pivoted together, the cassette being engaged between said second surface and said third surface when said beaks are pivoted toward each other.

17. A hand tool according to claim 16 wherein the protrusion extending from said first beak and the protrusion extending from said second beak, when pivoted together, define a contour surface that conforms to one edge of the cassette enabling the one edge of the cassette to lie against the contour surface.

18. A hand tool according to claim 17 wherein the contour surface is substantially flat.

19. A hand tool according to claim 17 wherein the contour surface is curved.

20. A hand tool according to claim 10 wherein at least one of the two longitudinal segments is at least equal to the length of the the peripheral edge of the cassette.

21. A device for securing a dental X-ray cassette, comprising:
(a) a first and a second elongated members each having a first and second end portions,
(b) a pivotal connecting means for pivotally connecting said first and second members, said connecting means being located between said first and second ends of said first and second members, respectively, wherein said first and second members are pivotable between a closed position where said first end portions of said first and second members are in substantial abutment, and an open position where said first end portions are separated, (c) complementary handle means defining said second end portions for pivoting said members,
(d) complementary beak elements defining said first end portions of said first and second members which define a substantially C-shaped cross-sectional configuration having a cross-sectional dimension substantially less than the length of said first end portions when said members are in the closed position,
(e) elongated trough means defined by said beak elements for securing a portion of an X-ray cassette recessed therein and disposed between said first and second end portions when said members are in the closed position.

* * * * *